(12) United States Patent
Sheffield

(10) Patent No.: US 9,835,526 B2
(45) Date of Patent: Dec. 5, 2017

(54) SYSTEMS AND METHODS FOR REMOVING CONTAMINATES FROM A STREAM PRIOR TO PASSING THE STREAM THROUGH AN ANALYZER

(71) Applicant: Kinetic Separation Technologies LLC, Texas City, TX (US)

(72) Inventor: Glenn Sheffield, Galveston, TX (US)

(73) Assignee: KINETIC SEPARATION TECHNOLOGIES LLC, Texas City, TX (US)

( * ) Notice: Subject to any disclaimer, the term of this patent is extended or adjusted under 35 U.S.C. 154(b) by 351 days.

(21) Appl. No.: 14/540,847

(22) Filed: Nov. 13, 2014

(65) Prior Publication Data
US 2015/0168274 A1 Jun. 18, 2015

Related U.S. Application Data

(60) Provisional application No. 61/903,683, filed on Nov. 13, 2013.

(51) Int. Cl.
| | |
|---|---|
| *G01N 1/22* | (2006.01) |
| *G01N 1/34* | (2006.01) |
| *B01D 45/02* | (2006.01) |
| *B01D 45/06* | (2006.01) |

(52) U.S. Cl.
CPC ............. *G01N 1/2205* (2013.01); *G01N 1/34* (2013.01); *B01D 45/02* (2013.01); *B01D 45/06* (2013.01); *G01N 1/2247* (2013.01); *G01N 2001/2282* (2013.01)

(58) Field of Classification Search
None
See application file for complete search history.

(56) References Cited

U.S. PATENT DOCUMENTS 3,759,087 A * 9/1973 Iwao .................... G01N 1/2247
55/523
4,772,454 A * 9/1988 Jarolics ................ G01N 1/2258
422/527

* cited by examiner

*Primary Examiner* — Benjamin M Kurtz
(74) *Attorney, Agent, or Firm* — Raymond R. Ferrera; Adams and Reese LLP

(57) ABSTRACT

A separator comprising: a first and second chamber, wherein the chambers are generally vertically disposed and parallel to each other; and the chambers have an upper end and a lower end; and the separator comprises an upper body and a lower body, wherein the upper ends are disposed in communication with the upper body, and the lower ends are disposed in communication with the lower body. Further disclosed is a single-chamber separator including a cooler. The cooler surrounds a portion of the chamber, and includes a coolant inlet disposed on a bottom surface, and a coolant outlet disposed on a top surface, and further includes baffles for directing coolant flow in a back and forth manner inside of the cooler. Also disclosed is a dual-chamber separator including a plurality of filters. The filters are disposed in the chambers in surrounding relationship to the tubes.

8 Claims, 9 Drawing Sheets

SYSTEMS AND METHODS FOR REMOVING CONTAMINATES FROM A STREAM PRIOR TO PASSING THE STREAM THROUGH AN ANALYZER

FIELD

The present invention relates generally to systems and methods for removing contaminates from a process stream, and in a particular though non-limiting embodiment, systems and methods for removing contaminates from a slip stream prior to passing the stream through an analyzer.

BACKGROUND

It is often necessary to analyze a process stream in a chemical or refining process. Typically, a process stream is analyzed by pulling a slip stream off of the process stream and then passing the slip stream through a process analyzer for analysis.

Proper conditioning of analyzer samples is the single most important maintenance consideration in an analyzer installation. Issues with the sample handling system are the largest maintenance problems with analyzers.

The basic criteria for a sample handling device is to deliver a representative sample which is compatible with the analyzer, with an acceptable response time, in a safe, reliable, and cost effective manner. A representative sample may vary from the exact composition of a sample stream within predetermined and acceptable tolerances.

Often times, contaminates and immiscible liquids, such as particulates and water, must be removed from the slip stream before passing it through the analyzer to prevent inaccurate readings and damage to the analyzer. Thus, at a minimum, most process analyzers require filtration. Because the filter must remove impurities without changing the composition of the sample, inert materials such as glass, stainless steel, ceramics, and fluorocarbon are generally used. A small filter housing designed for sample conditioning is typically used. Although the limited size maximizes filter element replacement, it is necessary to prevent excess lag time.

When filters alone fail to condition the sample, sample separators are employed in order to protect the analytical equipment from subsequent damage.

One separator type known in the art is a membrane separator. Membrane separators are devices employing a polymeric membrane. The membrane strips liquid from a sample gas. The separator directs a low flow, low pressure hydrocarbon process stream across a membrane. The hydrocarbon permeates the membrane. Liquids are repelled and exit through the return. However, common issues with membrane separators is that the membranes are typically submicron-rated, which do not tolerate particles in the process. A differential pressure greater than 15 psi will push the larger water molecules through the membrane.

Another separator known in the art is a knock-out separator. Knock-out-type separators are used to remove contaminates from gas samples. Knock-out separators reduce the flow of vapor, which allows the liquid droplets to separate by gravity. Some models of knock-out pots use baffles, which allow the vapor to impact the smooth surface and drain to the side of the enclosure. The primary objection to this type of device is that it requires relatively large bodies with limited flow, which creates excessive lag time that is prohibitive for many analyzer applications.

Another separator known in the art is a kinetic separator, which takes advantage of differing fluid densities to accomplish separation. A denser contaminant particle in a sample stream possesses a higher inertial force, rendering it less susceptible to dispersion due to pressure loss. Consequently, it continues in the flow stream while system pressure and flow path contours force the lighter components to flow toward a low pressure port above the sample outlet. Two-chamber separators use the second chamber as a polishing chamber. U.S. Pat. No. 6,444,001 to Sheffield is incorporated herein by reference in its entirety.

In a flowing process stream, the condensate and solid particulates in a gaseous sample, and the heavy immiscible liquids and solid particulates in a liquid sample, are not able to negotiate a 180 degree reversal of flow direction and will tend to remain in the fluid stream, while the lighter, more representative components will reverse direction and separate from the total contaminated stream and flow toward the lower pressure port. After separation, the kinetic separator returns the remaining sample to the original process stream, while the representative sample is sent to a polishing chamber where it will experience a second kinetic energy separation and filtration for further purification. The separator functions at full system pressure to optimize inertia while keeping the flow high, thus minimizing lag time. Unlike most conditioning devices, kinetic separators have also been found to function satisfactorily in low flow and low pressure applications with a minimal amount of lag time.

Typical kinetic separator bodies are manufactured from steel bar. However, they are very expensive to machine; cooling or heating the bodies is not practical; they require many expensive fittings; and the many fittings do not look aesthetically pleasing to the end user.

Additionally, with corrosive samples, exotic metals such as Hastelloy C and Monel are used for the separator body, in order to withstand harsh chemicals. However, doing so increases the manufacturing price by as much as five times that of a standard bar stock separator when using bar stock of the exotic metal. This price differential is due to the price of the metals, longer drilling time, and re-setup fees.

Furthermore, when slip streams are very hot, cooling the body of the separator is warranted. Cooling the body improves condensing, which helps to separate the condensables by lowering the dew point. This is particularly useful when the process is very close to saturation (i.e., 100% relative humidity). However, it is very difficult and expensive to cool a large mass of steel, as with the current monolithic bar stock bodies.

Frequently, single chamber filter housings are used in a heated sample conditioning panel. The panels are heated to prevent the sample from cooling to a temperature below the dew point. Often, unanticipated and undesirable impurities are imported with the sample. This portion of the sample is much heavier with a much higher dew point than the anticipated sample, and can create a liquid/gas dual phase product which is unacceptable to process analyzers hardware and detectors.

Furthermore, another issue with separators known in the art is that the single pore size filters typically supplied with the separators are quickly overwhelmed. Very heavily contaminated product is encountered in applications such as water and catalyst dust, causing the filters to quickly fill. Even rugged edge type stainless steel filters have limited range. Currently the solution to this problem is to utilize a bank of large sock type filters, which is expensive and prohibitive because of the long lag time, expensive filter replacement cost, man hours involved, and exposure of personnel to hazardous chemicals associated with it.

Filter housings typical in this industry have one filter. They are sometimes put in parallel to facilitate a redundant configuration to allow a filter change to occur while the other housing continues to filter the product. Even more occasionally, two housing with the same pore size filters are put in parallel to increase the surface area to handle a particularly heavy particulate loading in a given application.

However, it is often difficult to choose an appropriate pore size for a particular application. The recognized standard micron ratings used for most analyzer applications is 2 or 15 micron. With only one to choose, the decision is either a filter that will remove most of the contaminates and last an acceptable time, or a filter that will remove much more of the contaminates, but must be changed more often.

There is, therefore, a long-standing but unmet need for systems and methods for removing contaminates from a slip stream before the stream is fed into a process analyzer, in a more cost effective and time efficient manner, and in which one system could be used in a variety of applications.

SUMMARY

A separator for removing contaminates from a sample is disclosed, including at least: a first chamber and a second chamber, wherein the first chamber and second chamber are generally vertically disposed and parallel to each other. Each of the chambers include at least an upper end and a lower end. The separator further includes at least an upper body and a lower body, wherein the upper ends of the chambers are disposed in communication with the upper body, and the lower ends of the chambers are disposed in communication with the lower body.

Also disclosed is a kinetic separator including at least: a chamber, the chamber including at least an upper end and a lower end and a lower outlet and an upper outlet, wherein the lower outlet is disposed generally at the lower end of the chamber, and the upper outlet is disposed generally at the upper end of the chamber. A chamber inlet is disposed in communication with the chamber, and includes a tube having an open end received in the chamber. The tube is capable of directing a fluid entering the chamber toward the lower end of the chamber. The separator further includes at least a cooler. The cooler surrounds a middle portion of the chamber, and includes a coolant inlet disposed on a bottom surface of the cooler, and a coolant outlet disposed on a top surface of the cooler, and further includes baffles for directing coolant flow in a back and forth manner inside of the cooler.

Also disclosed is a separator for removing contaminates from a sample, including at least a first chamber and a second chamber, wherein the first chamber and second chamber are generally vertically disposed and parallel to each other. Each of the chambers include at least an upper end and a lower end. A first chamber inlet is disposed in communication with the first chamber, and includes a first tube having an open end received in the first chamber. A second chamber inlet is disposed in communication with the second chamber, and includes a second tube having an open end received in the second chamber. A plurality of first filters are disposed in the first chamber in surrounding relationship to the first tube; and a plurality of second filters are disposed in the second chamber in surrounding relationship to the second tube.

BRIEF DESCRIPTION OF THE DRAWINGS

FIG. 2 further illustrates the route of the coolant after it absorbs the heat of the process and reheats the slip stream sample exiting the separator, according to example embodiments.

DETAILED DESCRIPTION OF SEVERAL EXAMPLE EMBODIMENTS

Hybrid Tube/Machined Separator Embodiments

Figure 1:
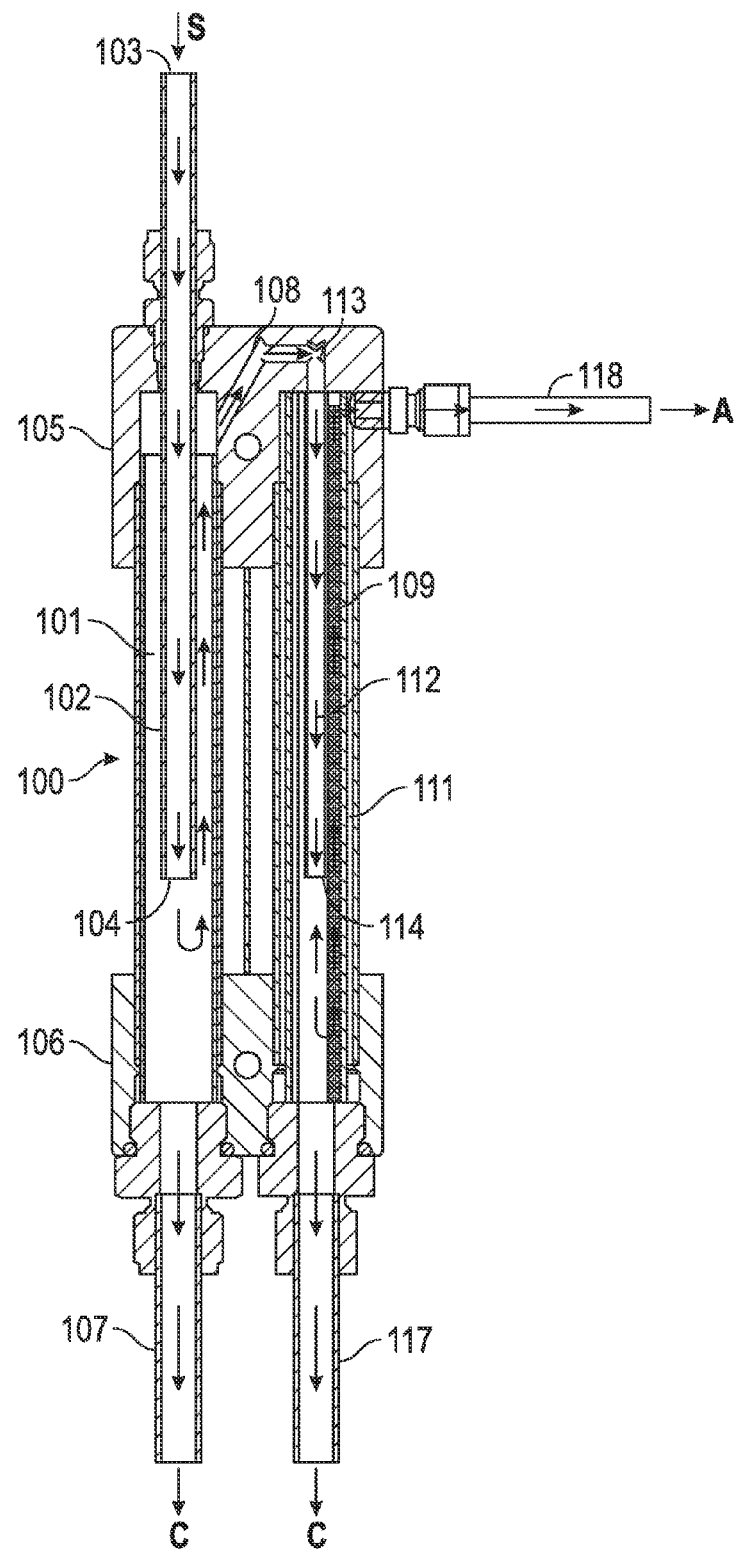
FIG. 1 illustrates a side sectional view of a separator according to an example embodiment.

An example embodiment which eliminates the need for a monolithic steel bar body is illustrated in FIG. 1. In further example embodiments, several fittings, a seal, a spring, a tubing cap, and other elements required in embodiments utilizing a monolithic body are unnecessary, resulting in reduced costs and maintenance time in operating the separator.

According to example embodiments, the separator 100 is capable of handling a wide range of temperatures and pressures. In other embodiments, the separator 100 is built with stainless steel chambers 101, 111 welded between two stainless steel bodies 105, 106, top and bottom, respectively. The separator 100 is manufactured in varying sizes, but according to one example embodiment, 1" stainless steel tubing and two stainless steel bodies are used to simulate a standard 12" long separator.

The sample enters the separator system 100 (in the direction shown by arrow S) at the first inlet 103 of the first tubing 102. The diameter of the first tubing 102 is smaller than the diameter of the first chamber 101, so that the first tubing 102 fits inside of the first chamber 101. The sample passes through the first tubing 102 to the first outlet 104. The first outlet 104 is located inside of the first chamber 101. Gravity, inertia, and cooling (such as internal cooling caused by expansion of gases) cause kinetic separation of the sample, separating the slip stream which contains the representative process components from the heavier contaminants. Contamination and water "drops out" of the sample, and flows downward through the lower part of the first chamber 101, exiting the separator system 100 at the first return line 107 (represented in the figure as C).

According to example embodiments, the condensate and solid particulates in a gaseous sample, and the heavy immiscible liquids and solid particulates in a liquid sample, are not able to negotiate a 180 degree reversal of flow direction and tend to remain in the fluid stream, while the lighter, more representative components will reverse direction and separate from the total contaminated stream and flow toward the lower pressure port. After separation, the kinetic separator returns the remaining sample to the original process stream, while the representative sample is sent to a polishing chamber 111 where it will experience a second kinetic energy separation and filtration for further purification.

Due to system pressure, the remainder of the sample (containing the representative process components) flows upwardly into the top part of the first chamber 101, and enters the connection line 108. The connection line 108 connects the first chamber 101 to the second inlet 113 of the second tubing 112. The diameter of the second tubing 112 is less than the diameter of the second chamber 111, so that the second tubing 112 fits inside of the second chamber 111. The sample enters the second tubing 112 at the second inlet 113. The sample passes through the second tubing 112 to the second outlet 114. The second outlet 114 is located inside of the second chamber 111. Contamination and water "drops out" of the sample, and flows downward through the second chamber 111, exiting the separator system 100 at the second return line 117 (represented in the figure as C).

First return line 107 and second return line 117 join at a common low-pressure return (not shown). In some embodiments, the second chamber 111 employs a flow meter to control at the optimum sample flow rate.

The remainder of the sample flows upwardly in the second chamber 111, and passes through one or more filters 109, before exiting at the analyzer feed line 118 (represented in the figure as A). Filters 109 are customized to target specific contaminants. For example, a filter is used to coalesce mist or condensate and remove particulate from a gas stream. In some examples, filters 109 remove free water and solid particles from a liquid hydrocarbon process. In further example embodiments, the filters 109 are 316 stainless steel woven wire filters for back flush applications with stack or water samples. In certain embodiments, the flow passes vertically though the filters, which impacts the filter element at a shallow angle. This combined with momentum of the flow has a self-cleaning effect.

In other example embodiments, filters are used in the first chamber 101.

According to still further embodiments, the upper steel body 105 is 3" wide×3" tall×1.5" thick, while the lower steel body 106 is 3" wide×2" tall×1.5" thick.

Example embodiments eliminate the monolithic body typically found in known kinetic separators.

According to still further embodiments, kinetic technology performance is improved by utilizing a polished surface that separates contaminants and water more efficiently than a rough surface. Water has a high surface tension due to intermolecular cohesive attraction. Polymers such as PTFE Teflon® have a very low coefficient of friction. According to example embodiments, the inside chamber(s) of a kinetic separator are lined with PTFE Teflon®, thus improving separation at low flow rates. At high flow rates, the low surface friction of the PTFE Teflon® allows the condensate to traverse the length of the inner wall without defusing to smaller droplets. This also allows the solid contaminants to move through unobstructed without sticking or adhering to the chamber walls.

In other embodiments, the smaller bodies mean less bar stock is needed, and drilling time is reduced. According to still further embodiments, exotic metal tubing is used.

In still other embodiments, the chambers and corresponding filters are aligned in a parallel arrangement. Such an arrangement is useful in applications where the impurities can be adequately filtered with one pore size rather than a dual filter with graduated pore size (i.e., the range of impurities runs from particle sizes 15 to 50 micron, which would make the 2 micron second filter useless, or vice versa, with the particle size ranging between 3 and 10 micron, which would not be removed by the first 15 micron filter). This results in a significant improvement in run time between filter changes.

In embodiments utilizing the parallel arrangement, a sealed chamber is created in the first chamber.

To complete the parallel configuration embodiments, there is a return route for the filtered sample from the first chamber to the analyzer exit port. Regardless of the loading in either chamber, as the filters become obstructed the product will seek the path of least resistance until both are completely plugged.

Hybrid Tube/Machined Separator With Cooler Embodiments

Figure 2:
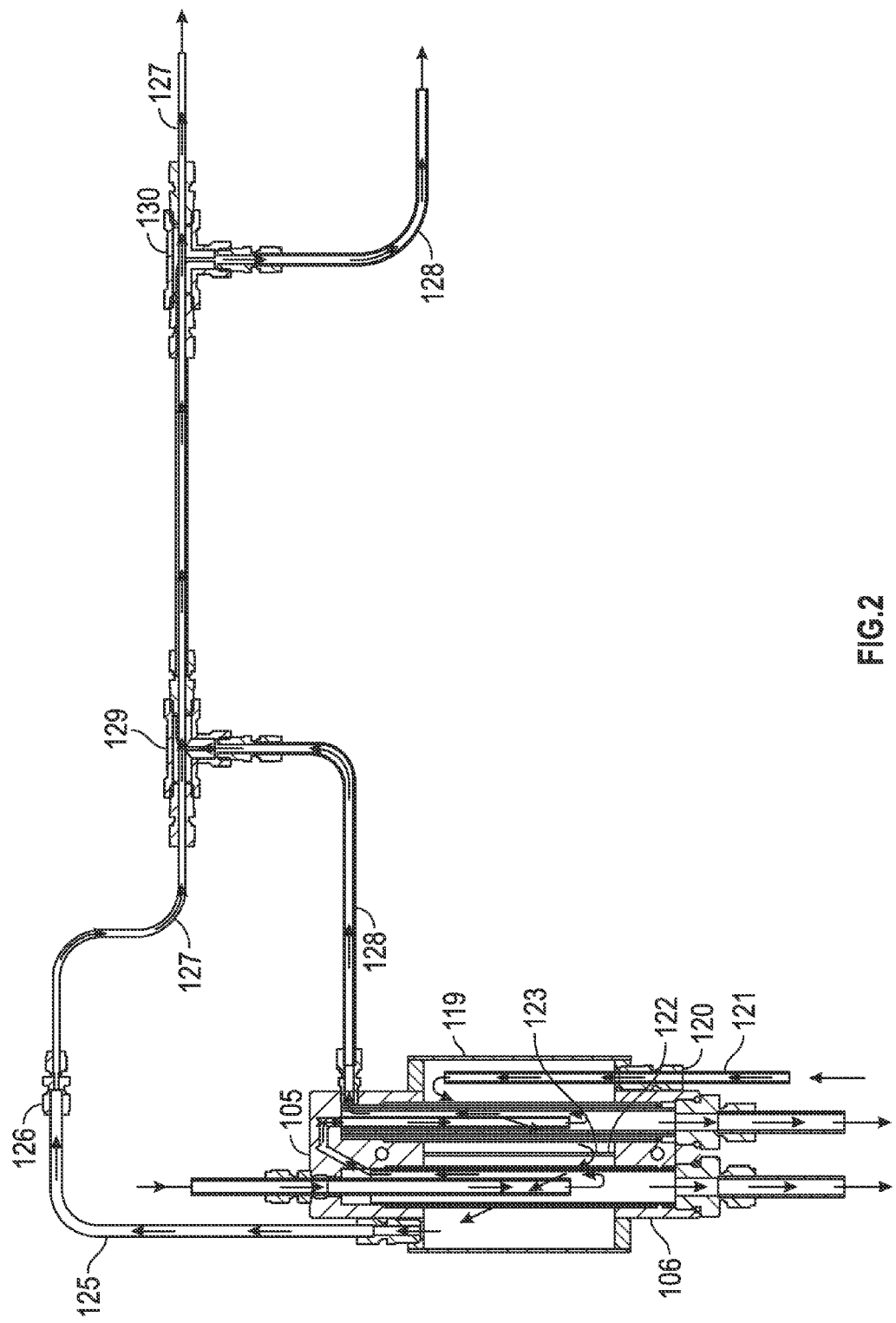
FIG. 2 illustrates a side sectional view of an example embodiment, incorporating a cooler for cooling the sample stream as it passes through the kinetic separator.
Figure 3:
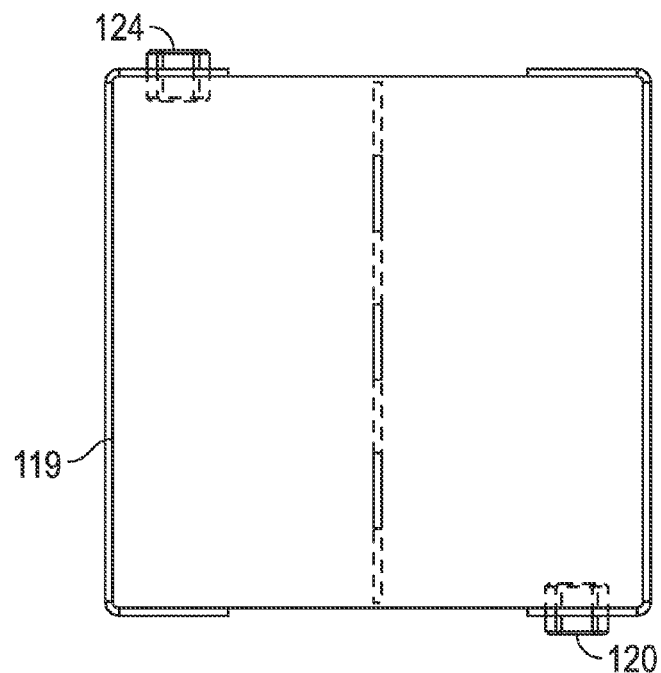
FIG. 3 illustrates a side view of a welded cooler body, according to an example embodiment.
Figure 3A:
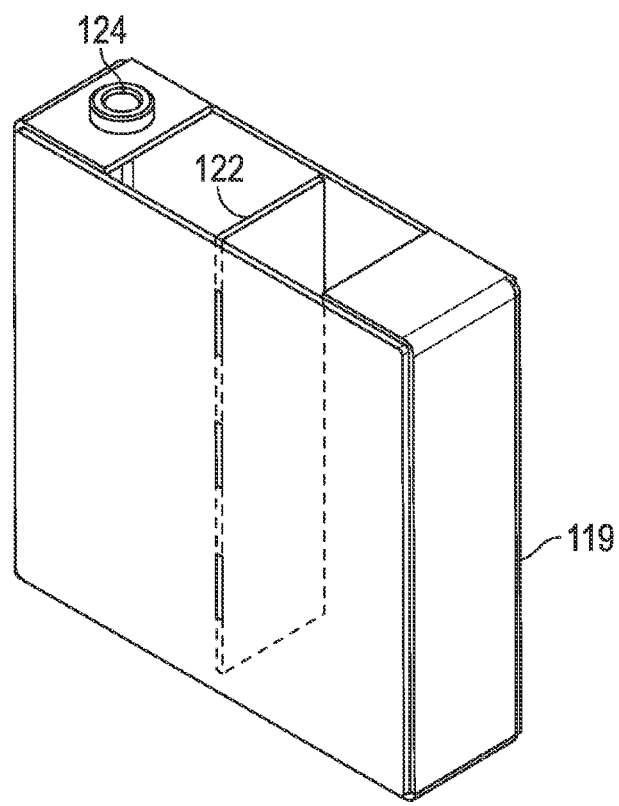
FIG. 3A illustrates a front perspective view of the welded cooler body from FIG. 3, according to an example embodiment.

Turning now to FIGS. 2, 3, and 3A, a cooler 119 according to an example embodiment employs 2-4" long by 2.0" wide by ¼" thick pieces of stainless steel plates. In certain embodiments, these plates are welded onto the top and bottom bodies 105, 106 before welding the chambers 101, 111 and tubing 102, 112 into the corresponding holes. Two holes are also drilled and threaded to ¼" NPT on the outside corners of each plate. The bottom ¼" NPT hole 120 on the right side serves as an inlet for the coolant supply tube 121. The flow of coolant is forced to the uppermost end of the cooling chamber 119 by using a ¼" bored through fitting and inserting a ¼" coolant supply tube 121 into the uppermost part of the cooler housing. In example embodiments, the outside of the cooler 119 is stainless steel sheet metal.

In still other embodiments, the cooling chamber is divided into two chambers by welding a divider 122 of stainless steel sheet metal in the middle parallel to the tubing. In further embodiments, a ½" hole 123 in the first sealed chamber is located at the bottom of this divider. This hole 123 and divider 122 creates a flow path from the top of the cooler (second) chamber, to the bottom of the same chamber, through the ½" hole, upwards through the warmer (first) chamber and out the uppermost ¼" NPT fitting and cooler opening 124. The purpose of the flow path is to force the coolant to flow over the entire length of both sample tubings, and encounter the hottest section last.

Furthermore, this flow pattern prevents the coolant from being heated immediately upon entering the cooler and distributing hot coolant through the rest of the chambers. Also, the second chamber is the polishing chamber, which will benefit the most from the cooler temperature. Besides the fact that it is meant to get the last chance condensables, the second chamber also has a much higher area expansion than the first chamber, thus forcing the smaller droplets to condense, i.e., if there are light condensables left, this is where the maximum cooling will occur.

According to example embodiments, a 1" outer diameter chamber and a ¼" inner diameter of the ⅜" outer diameter tube in the first chamber, the approximate area expansion is 16 times. In the second chamber, with a ¼" tube and a ⅛"

inner diameter the approximate area expansion is 64 times. The big difference is the cooling created when dealing with typically light gases such as hydrogen.

In other example embodiments, the sheet metal for forming the cooler is cut in such a fashion as to fold together like a shipping box with flaps on the ends to allow for an extended area on the ends to weld the couplings for the ¼" NPT fittings.

According to still other embodiments, the separator is less expensive to manufacture, as opposed to drilling two holes through a monolithic steel body. Furthermore, stainless steel tubing transfers heat more efficiently than bar stock.

In embodiments where extreme heating or cooling is required, the separator is constructed of tubing with fins on the outside walls.

Further, in still other embodiments, the tubing increases the separator's pressure rating by merely increasing the rating of the tubing.

According to still other embodiments, the sample is cooled in order to aid condensing, which assists in dropping the sample's dew point. This allows the sample to maintain a single phase state, which is important for the analyzer to function.

In further example embodiments, upon exiting the separator, the sample is re-heated to prevent the sample from re-condensing (i.e., dropping below the dew point as it flows to the analyzer). Doing so prevents a two-phase sample from entering the analyzer.

According to example embodiments, as shown in FIG. 2, a tube 125 is routed from the cooler exit to the other side of the separator to the analyzer. Even though the condensables have been removed from the sample stream, if the sample temperature is reduced, there is a possibility of further condensation if the temperature falls below the dew point. Thus, in example embodiments, the hot coolant created in the separator is put in a reduced size of tubing, wrapped around the analyzer tubing, and insulated.

In other embodiments, a bored-through tee fitting 129 is used. The exiting coolant tubing 125 is reduced to a smaller size tubing 127 using a reducing union 126. The reduced tubing is sealed with a nut and feral. This tube is threaded through the inside of the larger sample tubing 128. The larger tube 128 is supplied from the branch side of the tee 129 with the heated gas. As the smaller tube 127 is inside the larger tube 128, it is heated the entire length of the run. Near the end of the run, another bored-through tee 130 allows the smaller tube 127 to exit the tee 130 with a nut and feral tube fitting, and the coolant exits the branch and is routed to a control device such as a needle valve or rotameter i.e., a tube in tube cooler.

According to other example embodiments, heated coolant tubing is placed inside the larger analyzer tubing, similar to a heating coil. In example embodiments, using the smaller analyzer tubing placed inside the larger heating tubing results in the outer most surface of the heated tubing to release heat into the atmosphere which is amplified due to the excellent heat exchanging properties of stainless steel. According to alternative embodiments, by submersing the smaller tubing in the larger tube with the sample, all of the heat is released to the process.

In still other example embodiments, a cooler has two distinct chambers that do not interact with each other. One cooling chamber is for the first chamber while the second cooling chamber is for the second separator chamber. Each cooling chamber has its own isolated path, and the coolant used for each of the cooling chambers is different, in some embodiments. In certain embodiments, the second cooling chamber coolant is instrument air, chilled water, or air from a vortex cooler.

Figure 8:
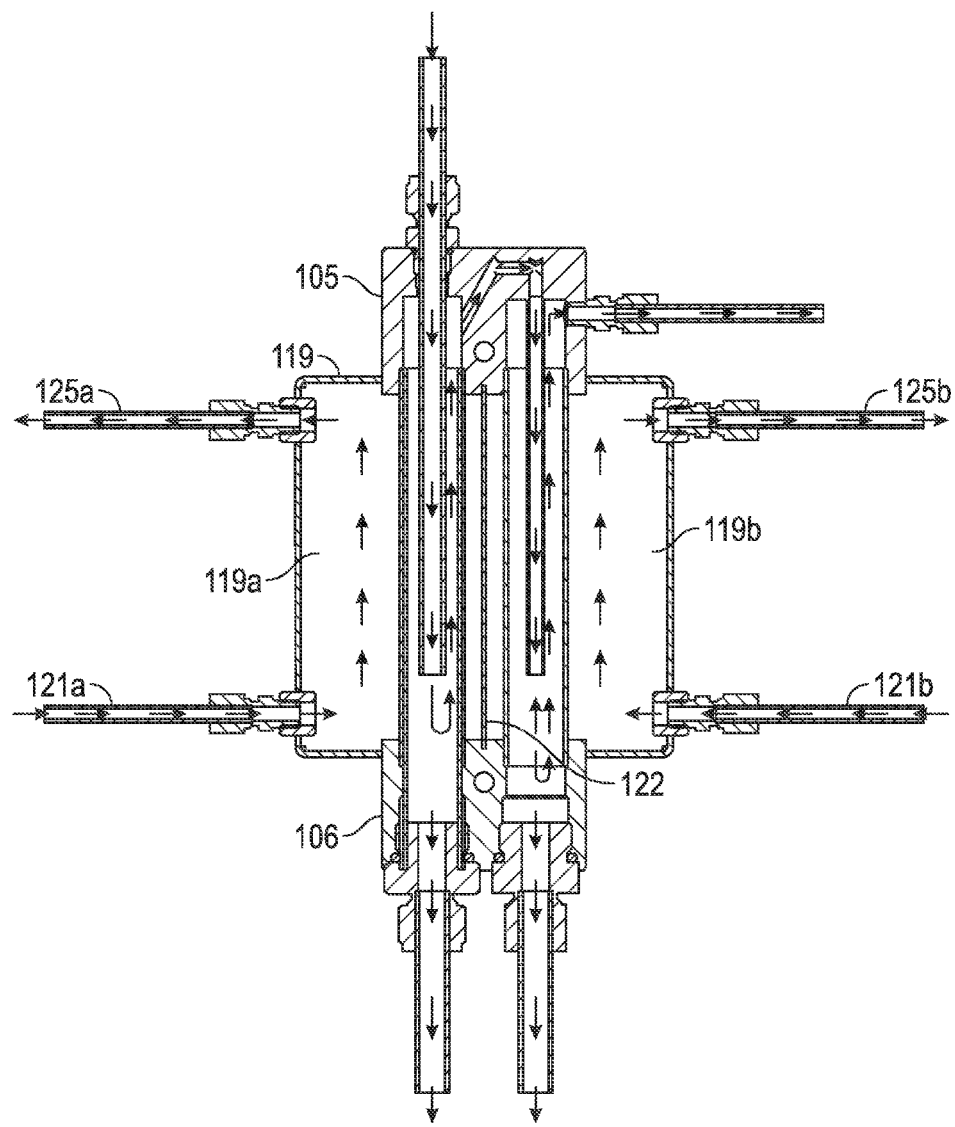
FIG. 8 illustrates a side sectional view of an example embodiment, incorporating a cooler with two distinct chambers for cooling the sample stream as it passes through the kinetic separator.

Turning now to FIG. 8, a cooler 119 according to an example embodiment has two separate cooling chambers 119*a* and 119*b*. In still other embodiments, the cooling chamber is divided into two chambers by welding a divider 122 of stainless steel sheet metal in the middle parallel to the tubing. There is a coolant supply tube 121*a*, 121*b* and a coolant exit tube 125*a*, 125*b* for each of the cooling chambers 119*a*, 119*b*, respectively.

Dual Stacked Chambers Separator Embodiments

Figure 4:
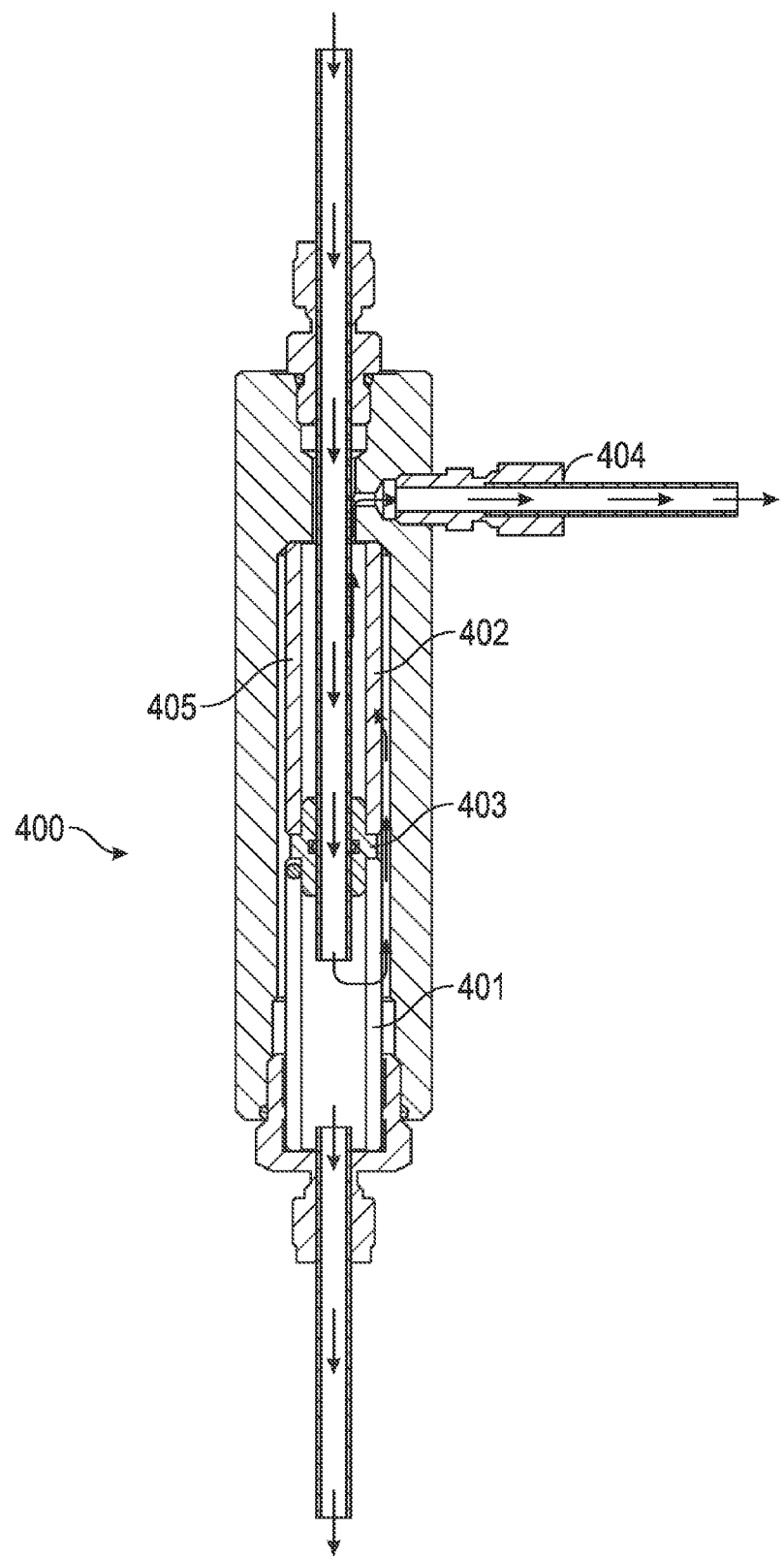
FIG. 4 illustrates a side sectional view of a separator according to another example embodiment, which utilizes a dual stacked chambers separator with stacked filters.

As illustrated in FIG. 4, due to the abundance of filter housings with standard 2.25" filters, example embodiments conform to those specifications. Standardizing is done to allow one brand and type of filter housing or filters to be compatible with other like devices.

According to certain embodiments, the separator configuration 400 shown in FIG. 4 is a direct replacement to existing single chamber 405 filter housings. Example embodiments do not require extra tubing or another rotameter (flow controller).

In still further embodiments, filters in series 401, 402 are used. According to example embodiments, providing filters with varying pore size, i.e., a filter with coarse pores and then a filter with fine pores in series, allows for less filter changes due to splitting the filtering load. In other example embodiments, the separator is also aided by the kinetic effect, thereby removing most of the particulates before it encounters the filter (flushed out the bottom). According to example embodiments, the kinetic energy separation also removes any condensables which were missed by upstream sample conditioning devices, as well of the possibility of condensing again due to temperature changes after conditioning.

In still other embodiments, the housing accommodates additional filters by putting Teflon® seals between each filter, i.e., additional filters are added to either side of the center sealing device 403. According to certain embodiments, these seals are Teflon® washer-type devices which allow communication between the inner parts of the filters, and seal the filter material from the outside surroundings until it permeates the filter.

According to further embodiments, a strait fitting at the bottom is counter-bored to allow the bottom filter 401 to protrude outside the housing. In this fashion there is no need to use a tool to retrieve spent filters.

In other embodiments, the middle sealing device 403 prevents communication between the different filters on either side with an internal grove, which houses an o-ring to seal against the protruding tube. Flow is allowed on the outside for communication between the inside to outside path of the bottom filter 401 to an outside to inside path to the upper filter 402, and then out the analyzer port 404. According to example embodiments, this seal fits tightly within each filter and has ridges to ensure that it is installable and removable.

According to example embodiments, the separator 400 uses industry standard 2.25" filters. In still further embodiments, the separator accommodates varying filter lengths by adjusting the depth of the chamber.

In other embodiments, the initially encountered coarse filter is replaced more frequently than the finer filter. Thus, in example embodiments, the filter configuration is tailored to have more and/or longer, coarser filter(s) followed in series with fewer and/or shorter, finer pore filters. Accordingly, in example embodiments, the filters last longer by more evenly predicting particulate saturation.

In still further embodiments, a plurality of filters is used in the chamber.

According to example embodiments, a plurality of filters is used in order to clean a very dirty sample. In example embodiments, the first lower filter is a highly condensed stainless steel woven wire filter with an inside pore size of 100 micron to an outside exit pore size of 40 micron. The sample is then routed to the outside of the next filter which, according to example embodiments, is a 15 micron filter. The sample is then routed from inside a common path from the inside of filter 2 to the inside of filter 3 and then to the outside of filter 3. The top of filter 3 is sealed to the uppermost smooth surface of the main chamber. The effluent exits the filter wall (in-out) and flows to the uppermost analyzer exit port.

In still further embodiments, if the sample has a substantial, heavy, coarse particulate, a longer stainless steel filter is used. In other embodiments, if the particulate is very heavy, but fine, a denser stainless steel filter is used.

In embodiments where a standard length is not possible because of the number or dimensions of the customs filter configuration, a body with a longer chamber is used. According to example embodiments, the bottom end is loosely fitting, allowing the filter to be easily removed. The uppermost protrusion is the same size, and fits into the center of a spring sized to maintain a constant pressure on the filters and thus maintain the seal.

In other embodiments, the spring sizes can vary to accommodate varying lengths caused by multiple combinations of filters.

In still other embodiments, the uppermost seal has an extended middle section to fill the void when the filter length is short, in order to fill the space which would cause excess lag time.

The length and pore size of the filters vary depending on the particular application, according to example embodiments. Filter choice is determined after a period of service by observing the amount of fouling on the individual filters. The filter most and least fouled are replaced to even the loading. This creates a custom specific fit for that particular application. This results in longer life and better filtration, which equals reduced maintenance cost and longer analyzer life.

Figure 5A:
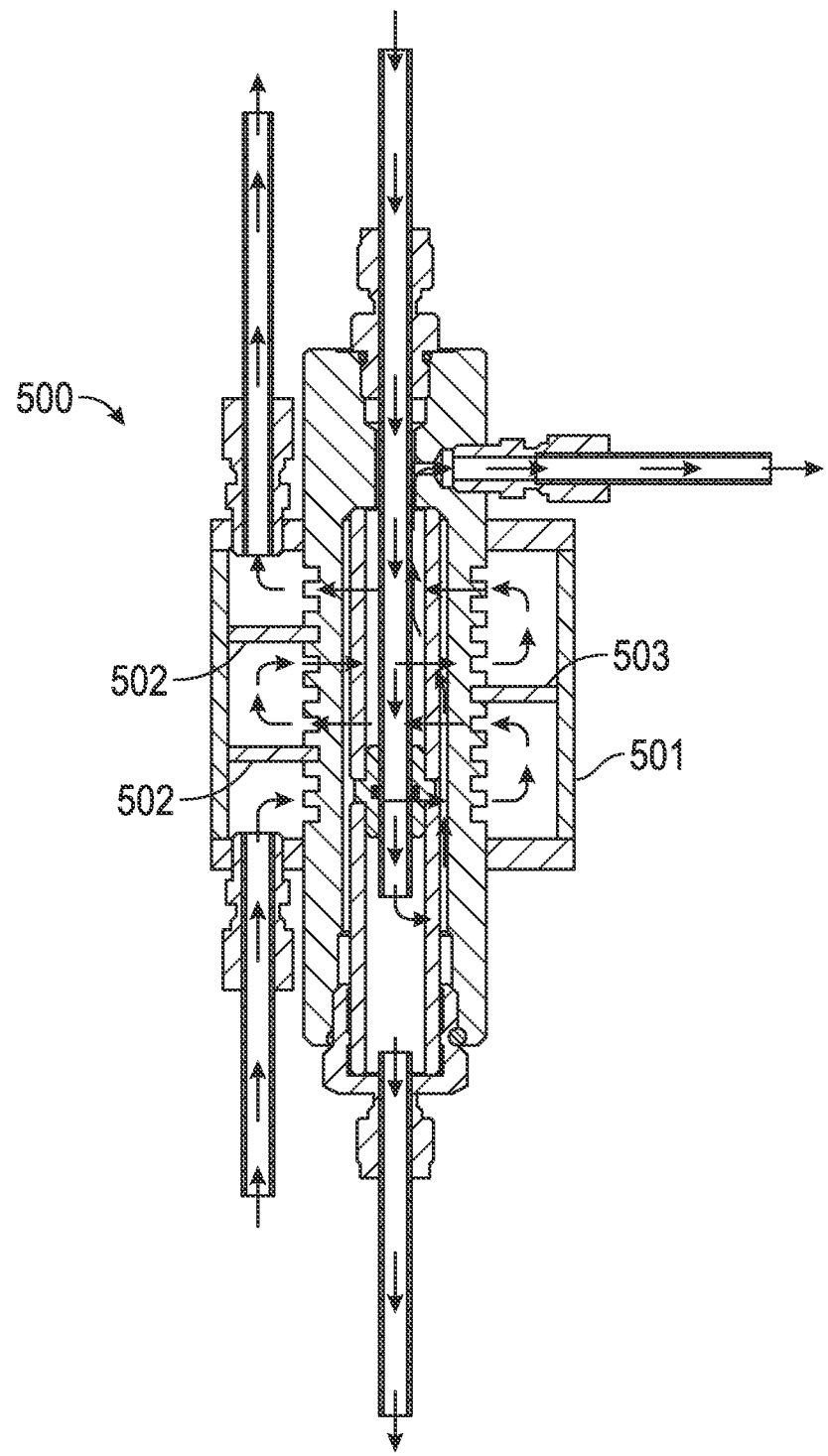
FIG. 5A illustrates a side sectional view of an example embodiment, which utilizes a separator and cooler with baffles.
Figure 5B:
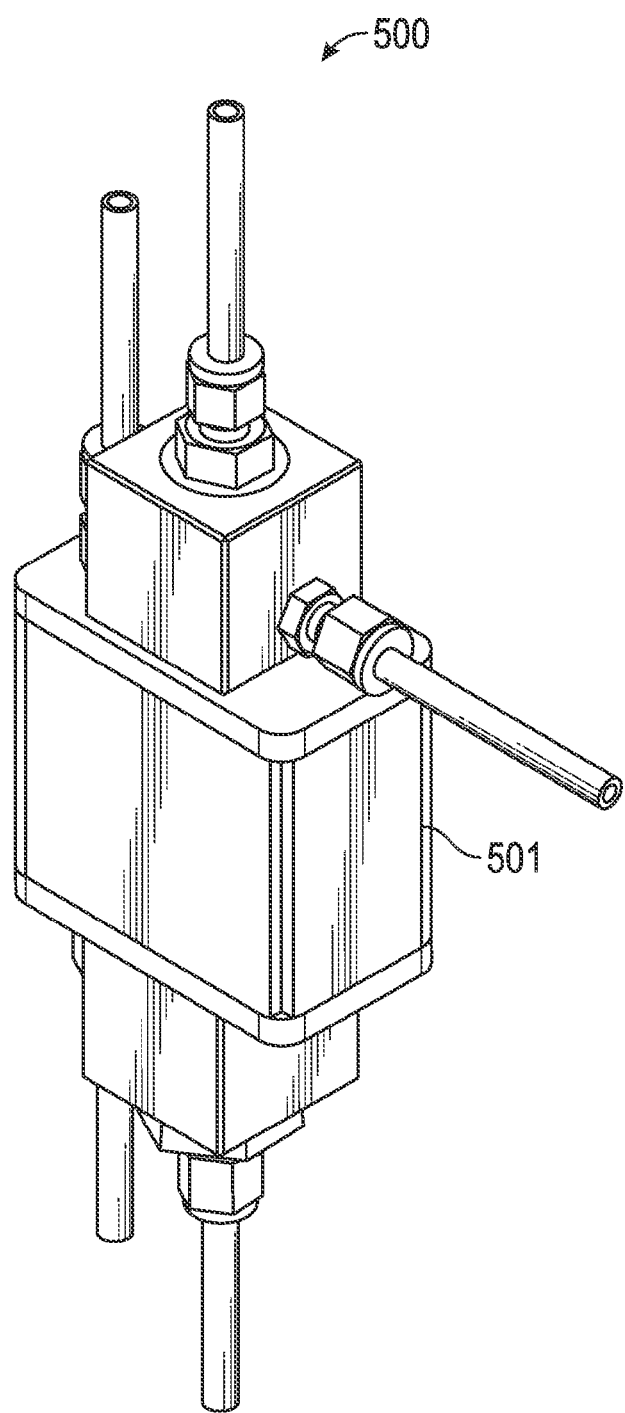
FIG. 5B illustrates a front perspective view of the separator and cooler from FIG. 5A, according to an example embodiment.

Single Chamber, Kinetic, Dual/Series/Stacked Filter Housing Embodiments With Cooler As illustrated in FIGS. 5 and 5A, in embodiments where a single chamber separator 500 is contained in a heated sample conditioning panel, a cooler 501 is used to lower the sample temperature below the dew point of the heavier contaminates, and the heavier contaminates are removed. In certain embodiments, an available, inexpensive medium, such as ambient instrument air or water, is used as a coolant in the cooler. According to still other embodiments, the light sample of interest is reheated in the heated cabinet before it reaches the analyzer.

According to example embodiments, the cooler 501 is a sealed box with baffles 502, 503 to direct the flow in a back and forth manner and aid in the transfer of heat. In other embodiments, the frame is composed of 2-3" long×2" wide× ¾" thick pieces of stainless steel. Each steel piece has a ¼" NPT hole drilled and taped as close to the end as practical. The plates have a square hole with a dimension slightly larger than the outer diameter of the filter housing. The plates are positioned slightly above the bottom of the housing and slightly below the analyzer exit port on the upper section and seam welded into place.

According to still other embodiments, baffles are placed on the upper third and on the lower third of the left side (502), as well as a baffle on the middle of the right side (503). The baffles are the proper size to fit the internal area of the cooler at that point. They are seam welded on the surface of the stainless sheet metal and seam welded at the top during final construction.

According to still further example embodiments, the body of the filter housing is square. The flat surfaces adjacent to the baffles match to form a continuously flat surface directing the flow of the coolant. Between these three areas, the corners of the square housing is serrated. There are $\frac{1}{16}$" saw blade type cuts evenly spaced between the baffles which allow the coolant to maintain contact with the body as the coolant flows. On the flat sides, the cuts where the sheet metal is stretched to fit has $4\frac{1}{8}$" deep cuts to allow the coolant to flow to the opposite side. All sections are seal welded to form a sealed container with an inlet and outlet.

In other embodiments, the body of the filter housing and cooler is insulated.

Back Flush Embodiments

Figure 6:
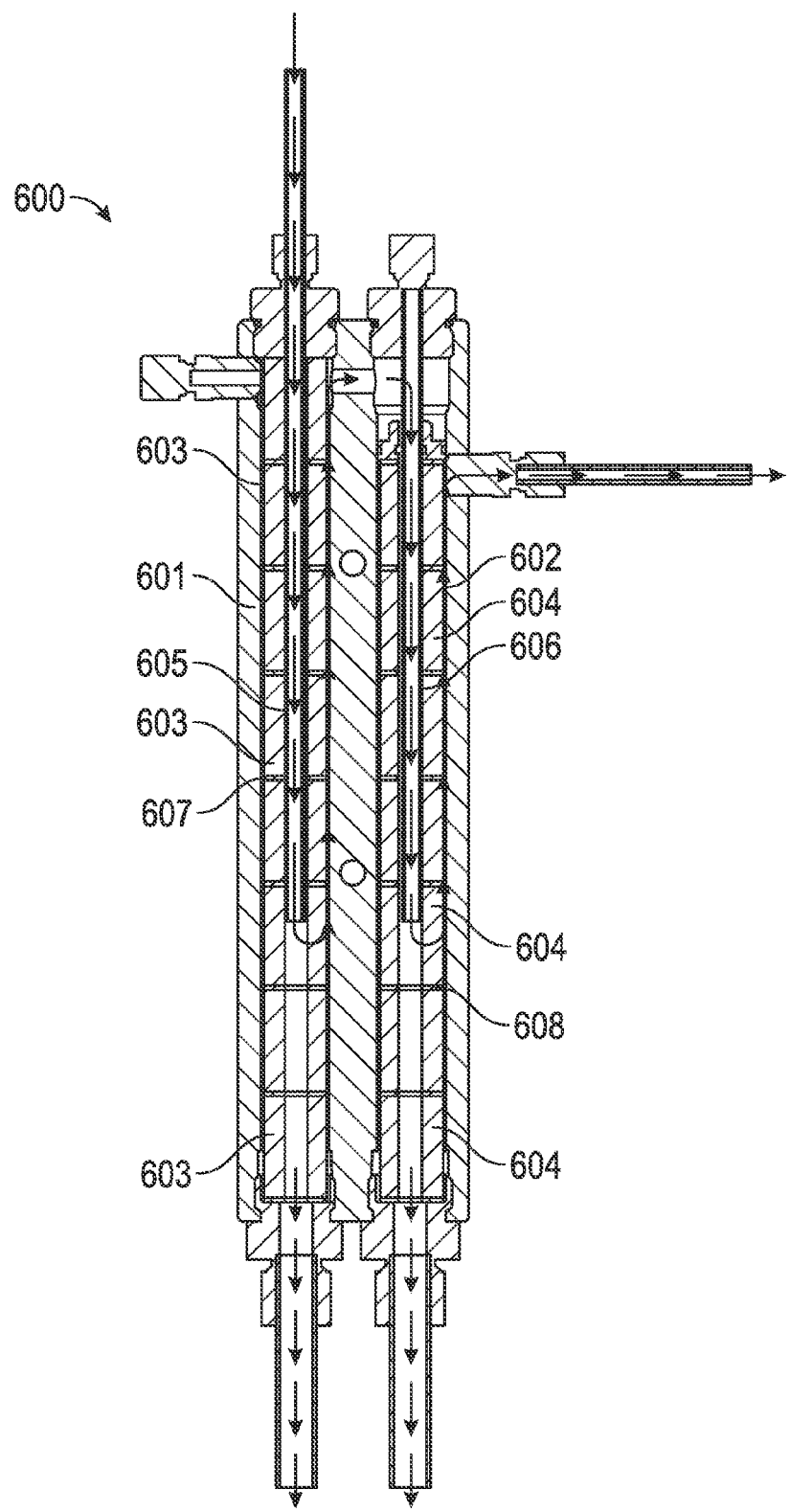
FIG. 6 illustrates a side sectional view of an example embodiment of a dual chamber kinetic separator with stacked woven wire filters, which utilizes a large surface area for a back-flush set-up, resulting in decreased turn-around time.

As shown in FIG. 6, according to example embodiments, modified, mist catcher-type filters are employed in a two-chamber separator 600. The filters comprise stainless steel wire woven to a specified depth, length, and width. In other embodiments, the filters are woven to a specified density which accounts for the pore size, i.e., an increase in density creates a finer pore size filter. In example embodiments, the modified filters have graduated density, from loosely woven inside to more tightly woven to satisfy the pore size specified on the outermost surface.

According to example embodiments, the filters have a high amount of surface area. The flow path is from the inside of the filters to the outside of the filters. The dual pore size allows the innermost cavities to be filled with the largest contaminates, while the finer contaminates travel farther before becoming lodged in a cavity of a similar dimension. In still further embodiments, an abundance of surface area allows most of the filter to be used, as opposed to a single layer filter of one pore size.

In example embodiments, the chambers 601, 602 are sized for multiple filters to be used. According to an example embodiment, the dimensions of a cylindrical filter are 1¼" long, ¾" in diameter, with a $\frac{5}{16}$" hole in the middle. The pore size of the example embodiment filter is 200 micron inside, to 75 micron exiting the filter. In other embodiments, in a second filter, the pore size is 75 micron inside to 55 outside exiting the filter. In still further embodiments, a filter with a 75 micron inside to a 45 micron outlet is used. According to further example embodiments, the pore size is adjusted by adding Teflon washers between the filters. When the fittings are tightened on the ends of the chambers, adding washers increases the pressure, and the density of the filters, resulting in finer pore sizes.

According to further embodiments, a short tube is used in either or both chambers, thus using the flow to rinse the (Teflon) sides of the filters for a self-cleaning effect.

In other embodiments, a long filter is used in either or both chambers, in order to give impurities of a size and weight that may be susceptible to change direction (spin off) to have less opportunity to do so and more opportunity to settle back down.

According to other embodiments, the flow through the chamber is adjusted so that it is 10 times the exit flow (to the other chamber or out to the analyzer, or both). Thus, it produces a slight angle which allows impurities to pass with less obstructions and thus less tendency to follow the flow to the side of the filter.

A further example embodiment is herein described. The filters 603, 604 are threaded onto the ¼" tubes 605, 606 in the chambers 601, 602. Between each filter is a Teflon® washer 607, 608 of a specified thickness. The washer is ¾" in diameter with a 5/16" hole in the center. Besides being used as an adjustment tool, the washers are employed to direct the flow of the sample and assure that there is not a partially unrestricted gap between the filters. As the suspended particulate flows down the unrestricted common (parallel) area between the filters, system pressure and flow path contours force it into the inner walls of the filters. As the varied internal paths are filled by the particulates corresponding to the assorted cavities, the entire length is subjected to the path of least resistance. As a chain of varying sizes of orifices are obstructed, the particulate flows over to the next path with a remaining exit flow, i.e., if a particle flows by an already plugged path, there will not be a flow, thus, no physical reason for it to continue in that direction. When it flows by an opening with a flow, it will gravitate to that location where it is subject to enter the path. If the remaining orifice is too small for the particle to enter its size, the flow through the center will push it to the next area or it will exit the chamber. As can be readily seen in FIG. 6, the kinetic effect will allow some of the particulate to exit the bottom without contacting the surface of the filter, thus acting as a pre-filter.

According to further example embodiments, woven wire mesh filters are improved by coating them with PTFE Teflon® to repel water and prevent particulate from sticking/lodging in the assorted mesh pores.

According to example embodiments, the flow path of the separator is suited to back flush the filters. Stainless steel wire woven filters are very expensive. Thus, the ability to back flush an application which is particularly contaminated is a significant advantage. In example embodiments, the back-flushing is done manually with valves, or, as in other embodiments, electronically with a differential pressure switch, solenoid valves, and a controller.

In other example embodiments, with extremely coarse process material, a redundant sample conditioning system is installed in conjunction with one automatic controller for both units.

Figure 7:
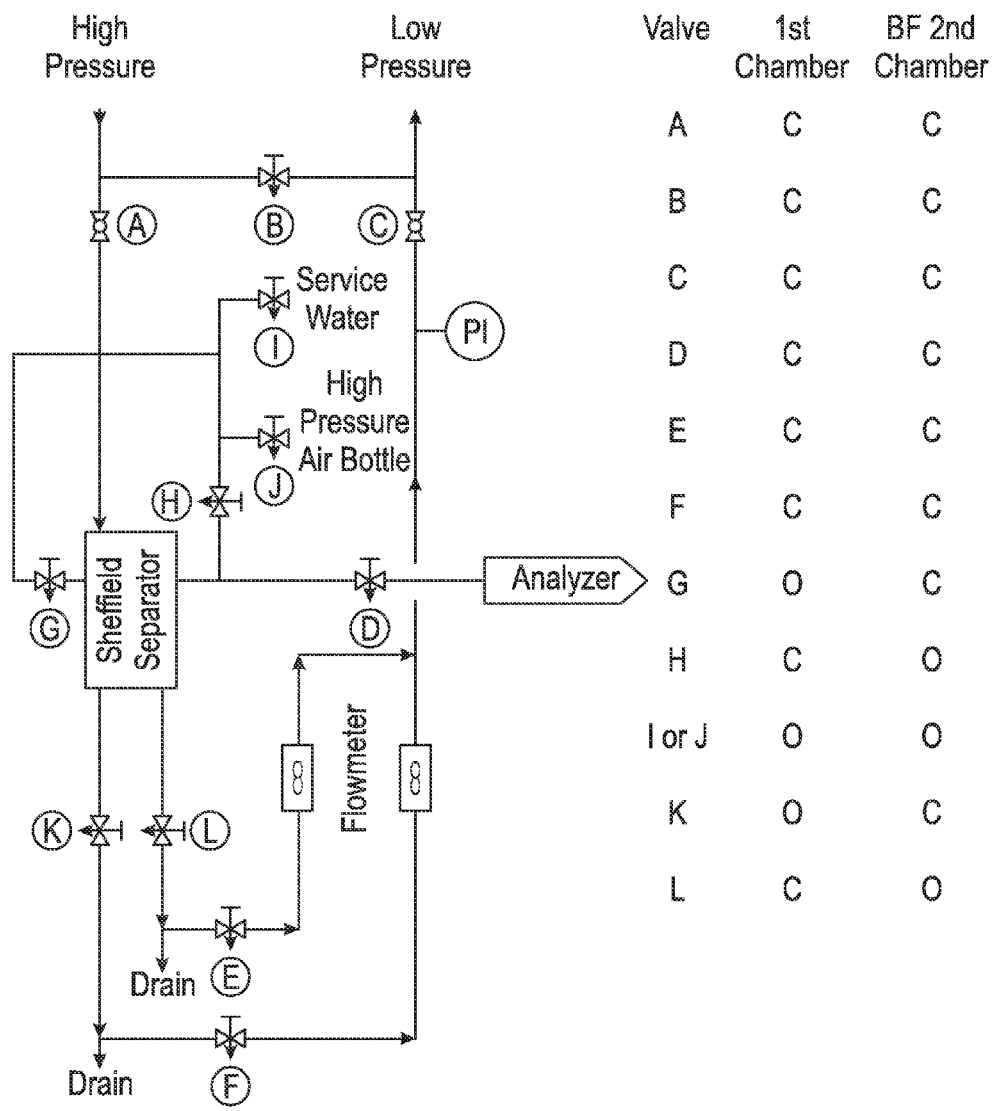
FIG. 7 illustrates example embodiments for back-flushing a kinetic separator, such as the example separator shown in FIG. 6.

FIG. 7 demonstrates an example embodiment of how the separator is isolated and the flow is reversed from an inside to outside orientation to an outside to inside orientation, with the effluent exiting the regular bottom exit port to the existing return. According to an example embodiment, Valve G is opened to allow valve I or J to supply back flush fluid to the first chamber, and valve D is closed and valve H is opened to allow valve I or J to back flush the second chamber. In example embodiments, the outside of the filters have the finest pore size, and, thus, are the most packed. The outside to inside back flush perpetuates the higher pressures being applied to the greatest obstacle. An alternate embodiment is to drill and tap holes on the outer sides of the separator. This assures a more even back flush. In certain example embodiments, service water is used for light build-ups, while in still other embodiments, 2,000 psi bottled gas is used for more stubborn blockages. All parts of the separator are specified to these pressures.

In addition to using tubing, the separator in other embodiments is designed with larger and longer chambers with the filters modified to fit, as well as using larger tubes. In still further embodiments, a third chamber is added if a second polishing chamber is needed to satisfy a specification for smaller particulates.

In still other embodiments, the dual chambers shown in FIG. 5 are modified to be used in parallel. The fitting on the top of the second chamber gains communication with the inlet tubing of the first chamber by using a tee. In still other embodiments, a Y configuration is used. The filtered sample in the second chamber combines with the filtered sample from the first chamber. Regardless of the loading in either chamber, as the filters become obstructed the product will seek the path of least resistance until both are completely plugged.

All separators herein described can be machined from multiple materials, including but not limited to: SS—Stainless Steel 316L, MN—Monel, HC—Hastelloy C, PTFE—Teflon®, KY—Kynar, and PVC—Polyvinyl Chloride.

The foregoing specification is provided only for illustrative purposes, and is not intended to describe all possible aspects of the present invention. While the invention has herein been shown and described in detail with respect to several exemplary embodiments, those of ordinary skill in the art will appreciate that minor changes to the description, and various other modifications, omissions and additions may also be made without departing from the spirit or scope thereof.

The invention claimed is:

1. A separator for removing contaminates from a sample, comprising:

a first chamber and a second chamber, wherein said first chamber and said second chamber are generally vertically disposed and parallel to each other, and each of said chambers comprise an upper end and a lower end;

an upper body and a lower body, wherein said upper ends of said chambers are disposed in communication with said upper body, and said lower ends of said chambers are disposed in communication with said lower body;

said first chamber having a first lower outlet and a first upper outlet, wherein said first lower outlet being disposed generally at said lower end of said first chamber, and said first upper chamber outlet being disposed generally at said upper end of said first chamber;

said second chamber having a second lower outlet and a second upper outlet, wherein said second lower outlet being disposed generally at said lower end of said second chamber, and said second upper chamber outlet being disposed generally at said upper end of said second chamber;

a first chamber inlet disposed in communication with said first chamber, said first chamber inlet comprising a first tube having an open end received in said first chamber, said first tube capable of directing a fluid entering said first chamber toward said lower end of said first chamber;

a second chamber inlet disposed in communication with said second chamber, said second chamber inlet comprising a second tube having an open end received in said second chamber, said second chamber inlet disposed in communication with said first upper chamber outlet, said second tube capable of directing separated fluid from said first chamber toward said lower end of said second chamber; and a cooler surrounding middle portions of said first chamber and said second chamber, said cooler comprising a top end and a lower end, wherein said top end is connected to said upper body and said lower end is connected to said lower body; further wherein said cooler has a coolant inlet disposed on the bottom of said cooler and a coolant outlet disposed on the top of said cooler.

2. The separator of claim 1, wherein said upper body and said lower body are made of stainless steel.

3. The separator of claim 1, wherein said first chamber and said second chamber are made of stainless steel.

4. The separator of claim 1, further comprising: a filter disposed in said second chamber in surrounding relationship to said second tube.

5. The separator of claim 4, further comprising a 316 stainless steel filter disposed in said second chamber in surrounding relationship to said second tube.

6. The separator of claim 1, wherein said cooler further comprises a divider, wherein said divider is located between said first chamber and said second chamber, and said divider comprises an opening at a lower end of said divider, so that coolant may pass from one side of said cooler to the other.

7. The separator of claim 1, wherein inner surfaces of said first chamber and said second chamber are polished.

8. The separator of claim 1, wherein said cooler is made of sheet metal.

* * * * *